(12) United States Patent
Sakata et al.

(10) Patent No.: US 11,125,659 B2
(45) Date of Patent: Sep. 21, 2021

(54) PRESERVATIVE SOLUTION FOR HEME PROTEIN, AND METHOD FOR STABILIZING HEME PROTEIN

(71) Applicant: EIKEN KAGAKU KABUSHIKI KAISHA, Tokyo (JP)

(72) Inventors: Kozue Sakata, Tochigi (JP); Shin Sugo, Tochigi (JP); Ryota Yasui, Tochigi (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 424 days.

(21) Appl. No.: 15/563,088

(22) PCT Filed: Mar. 31, 2016

(86) PCT No.: PCT/JP2016/060597
§ 371 (c)(1),
(2) Date: Feb. 6, 2018

(87) PCT Pub. No.: WO2016/159203
PCT Pub. Date: Oct. 6, 2016

(65) Prior Publication Data
US 2018/0172562 A1 Jun. 21, 2018

(30) Foreign Application Priority Data

Mar. 31, 2015 (JP) .............................. JP2015-070667

(51) Int. Cl.
*G01N 33/531* (2006.01)
*C07K 14/805* (2006.01)
*G01N 1/28* (2006.01)

(52) U.S. Cl.
CPC ............. *G01N 1/28* (2013.01); *C07K 14/805* (2013.01); *G01N 33/531* (2013.01)

(58) Field of Classification Search
CPC ....... G01N 1/28; G01N 33/531; C07K 14/805
See application file for complete search history.

(56) References Cited

U.S. PATENT DOCUMENTS

| | | |
|---|---|---|
| 5,094,956 A | 3/1992 | Grow et al. |
| 5,242,832 A | 9/1993 | Sakata |
| 6,376,169 B1 * | 4/2002 | Adams ................. C12Q 1/6883 435/4 |
| 7,354,732 B2 * | 4/2008 | Yonehara ................. C12Q 1/26 435/25 |
| 2008/0019871 A1 * | 1/2008 | Sakamoto ............... B01L 3/545 422/68.1 |
| 2010/0216178 A1 | 8/2010 | Sugo |
| 2011/0046052 A1 * | 2/2011 | Yang .................... A61K 9/0019 514/6.4 |

FOREIGN PATENT DOCUMENTS

| | | |
|---|---|---|
| CN | 101828112 A | 9/2010 |
| JP | 63-271160 A | 11/1988 |
| JP | 02-296149 A | 12/1990 |
| JP | 04-145366 A | 5/1992 |
| JP | 05-069466 A | 10/1993 |
| JP | 07-229902 A | 8/1995 |
| JP | 11-118806 A | 4/1999 |
| JP | 11-218533 A | 8/1999 |
| JP | 2000-258420 A | 9/2000 |
| JP | 2001-249132 A | 9/2001 |
| JP | 2003-014768 A | 1/2003 |
| JP | 2003-194825 A | 7/2003 |
| JP | 2009-097956 A | 5/2009 |
| JP | 2009-222710 A | 10/2009 |
| JP | 2013-257216 A | 12/2013 |
| WO | WO 2006/069246 A2 | 6/2006 |

OTHER PUBLICATIONS

Extended European Search Report in European Application No. 16773083.7, dated Aug. 6, 2018, pp. 1-5.
Office Action in China Application No. 201680030211.7, dated Jul. 1, 2019, 10 pages.

* cited by examiner

*Primary Examiner* — Tracy Vivlemore
*Assistant Examiner* — Nam P Nguyen
(74) *Attorney, Agent, or Firm* — Crowell & Moring LLP

(57) ABSTRACT

An object of the present invention is to provide a novel preservative solution for a heme protein and a method for stabilizing a heme protein, which are effective against denaturation or degradation of a heme protein, and the present invention specifically relates to a preservative solution for a heme protein comprising a disulfonic acid or a salt thereof, and a method for stabilizing a heme protein, which involves bringing a disulfonic acid or a salt thereof into coexistence in a sample comprising a heme protein.

8 Claims, No Drawings

PRESERVATIVE SOLUTION FOR HEME PROTEIN, AND METHOD FOR STABILIZING HEME PROTEIN

This application is a 371 application of PCT/JP2016/060597 having an international filing date of Mar. 31, 2016, which claims priority to JP2015-070667 filed Mar. 31, 2015, the entire contents of which are incorporated herein by reference.

TECHNICAL FIELD

The present invention relates to a preservative solution for a heme protein and a method for stabilizing a heme protein. The present invention particularly relates to a preservative solution for a heme protein and a method for stabilizing a heme protein, which are useful for immunoassay methods.

BACKGROUND ART

In recent years, a fecal occult blood test for detection of fecal blood has been broadly carried out as a primary test for colon cancer screening or a method for screening for a lower gastrointestinal disease, with the increasing incidence of cancer. The fecal occult blood test is conducted by a chemical measurement method based on a chemical coloring reaction employing the peroxidase-like activity of hemoglobin that is a heme protein or an immunoassay method employing a specific antibody against human hemoglobin. In particular the immunoassay method enables convenient and rapid measurement without the need of any dietary restriction and any restriction of drug-taking before the test, compared with chemical measurement methods, and therefore it becomes established as a major testing method for the fecal occult blood test.

However, hemoglobin is known to be very unstable in a solution and easily denatured or degraded. Such denaturation or degradation destroys hemoglobin conformation, resulting in decreased antigenicity. Therefore, the immunoassay method for measuring hemoglobin in such a case can produce erroneous measurement results. Examples of reasons of denaturation or degradation of hemoglobin are varied and include increased storage temperatures, the passage of time, bacteria and enzymes. For example, it is known with regard to storage temperatures that hemoglobin in a solution is relatively stable in a frozen or refrigerated state, but at room temperature or a temperature higher than the room temperature, denaturation or degradation of hemoglobin proceeds.

In particular, on a fecal occult blood test, feces are often collected by subjects themselves at their places, and are provided for the test by suspending the feces in a closed container containing a diluent for stool specimens. In such cases, fecal human hemoglobin may be left to stand in the solution for several days, or exposed to a high temperature during transportation via a transportation means such as a postal service. Also, a hospital or a clinical laboratory sometime takes a long time to have measurement results, since a large number of specimens and other test items are tested at such a facility. Under such circumstances, denaturation or degradation of hemoglobin tends to take place in a fecal occult blood test because of combined reasons such as a temperature rise and the passage of time.

Moreover, a fecal occult blood test often involves conducting measurement using an automatic analyzer capable of measuring many specimens accurately and rapidly. Upon measurement using an automatic analyzer, periodic calibration and precision control are performed for the automatic analyzer using a reference sample containing hemoglobin at a known concentration and a control sample containing hemoglobin at a known concentration, since changes in reagents and the analyzer affect the precision of the test results. Calibration involves measuring a reference sample containing a plurality of measurement target substances with known concentrations by an automatic analyzer, preparing a calibration curve, and performing calibration for the automatic analyzer. Precision control involves measuring a control sample containing measurement target substances with known concentrations by an automatic analyzer, and determining the analytical precision depending on if the measurement value is within a predetermined range. However, if hemoglobin contained in such a reference sample and a control sample is denatured or degraded, calibration and precision control cannot be performed accurately, leading to erroneous measurement.

Therefore, various methods for stabilizing hemoglobin have been proposed to suppress denaturation or degradation of hemoglobin so as to produce accurate measurement results. Examples of such methods that have been proposed include: a method involving adding antibacterial agents such as thimerosal and chlorhexidine (e.g., see Patent Literature 1); a method involving adding non-human animal hemoglobin (e.g., see Patent Literature 2); a method involving adding the sera of non-human animals (e.g., see Patent Literature 3); a method involving adding an glycosidase type bacteriolytic enzyme (e.g., see Patent Literature 4); a method involving adding sulfurous acid, disulfurous acid, or the like (e.g., see Patent Literature 5); a method involving adding acyl arginine esters and cationic surfactants (e.g., see Patent Literature 6); and a method involving adding glyoxalic acid (e.g., see Patent Literature 7).

Then, the applicant of the present invention has already proposed a method involving adding a water soluble transition metal complex such as a ferrocyan compound (e.g., see Patent Literature 8 and Patent Literature 9), a method involving adding an enzymatic degradation product of hemoglobin (e.g., see Patent Literature 10), a method involving adding transition metals (e.g., see Patent Literature 11), a method involving adding organic acid such as malic acid (e.g., see Patent Literature 12), a method involving adding delipidated albumin (e.g., see Patent Literature 13), and a method involving adding iminocarboxylic acid (e.g., see Patent Literature 14), for example.

However, hemoglobin is very unstable, so that even these methods for stabilizing hemoglobin are problematic in preventing denaturation or degradation of hemoglobin sufficiently.

CITATION LIST

Patent Literature

Patent Literature 1: JP Patent Publication (Kokai) No. 63-271160A (1988)
Patent Literature 2: JP Patent Publication (Kokai) No. 2-296149A (1990)
Patent Literature 3: JP Patent Publication (Kokai) No. 4-145366A (1992)
Patent Literature 4: JP Patent Publication (Kokoku) No. 5-69466B (1993)
Patent Literature 5: JP Patent Publication (Kokai) No. 2000-258420A
Patent Literature 6: JP Patent Publication (Kokai) No. 2009-222710A Patent Literature 7: JP Patent Publication (Kokai) No. 2013-257216A
Patent Literature 8: JP Patent Publication (Kokai) No. 7-229902A (1995)
Patent Literature 9: JP Patent Publication (Kokai) No. 11-118806A (1999)
Patent Literature 10: JP Patent Publication (Kokai) No. 11-218533A (1999)
Patent Literature 11: JP Patent Publication (Kokai) No. 2001-249132A
Patent Literature 12: JP Patent Publication (Kokai) No. 2003-14768A
Patent Literature 13: JP Patent Publication (Kokai) No. 2003-194825A
Patent Literature 14: JP Patent Publication (Kokai) No. 2009-097956A

SUMMARY OF INVENTION

Technical Problem

To solve such problems, an object of the present invention is to provide a novel preservative solution for a heme protein and a method for stabilizing a heme protein, which are effective against denaturation or degradation of a heme protein represented by hemoglobin.

Solution to Problem

The preservative solution for a heme protein of the present invention is characterized by containing disulfonic acid or a salt thereof. Furthermore, the method for stabilizing a heme protein of the present invention is characterized by bringing disulfonic acid or a salt thereof into coexistence in a sample containing the heme protein.

Specifically, the present invention encompasses the following (1) to (10).

(1) A preservative solution for a heme protein, containing a disulfonic acid or a salt thereof.

(2) The preservative solution for a heme protein according to (1), wherein
the disulfonic acid or a salt thereof has at least one of an open chain hydrocarbon group and a cyclic hydrocarbon group, and
the disulfonic acid or a salt thereof is at least one selected from the group consisting of:
a disulfonic acid or a salt thereof in which the open chain hydrocarbon group is a branched or linear hydrocarbon group and the main chain of the branched open chain hydrocarbon group or the linear open chain hydrocarbon group has any one of 1 to 10 carbon atoms;
a disulfonic acid or a salt thereof in which the cyclic hydrocarbon group is a cycloalkylene group or an aryl group and the cyclic hydrocarbon group has any one of 3 to 10 carbon atoms; and
a disulfonic acid or a salt thereof in which the cycloalkylene group or the aryl group has one or more substituted nitrogen atoms.

(3) The preservative solution for a heme protein according to (1) or (2), wherein the disulfonic acid or a salt thereof is at least one selected from the group consisting of methanedisulfonic acid, ethanedisulfonic acid, propanedisulfonic acid, butanedisulfonic acid, naphthalenedisulfonic acid, and piperazine-N,N'-bis(2-ethanesulfonic acid) or a salt thereof.

(4) The preservative solution for a heme protein according to any one of (1) to (3), wherein the concentration of the disulfonic acid or a salt thereof is 0.001 mol/L or more and 0.3 mol/L or less.

(5) The preservative solution for a heme protein according to any one of (1) to (4), further containing N-(2-hydroxyethyl)piperazine-N'-ethanesulfonic acid.

(6) The preservative solution for a heme protein according to any one of (1) to (5) further containing a heme protein, which is used as a reference sample or a control sample.

(7) The preservative solution for a heme protein according to any one of (1) to (6), which is used for immunoassay.

(8) A method for stabilizing a heme protein, wherein a disulfonic acid or a salt thereof is brought into coexistence in a sample containing a heme protein.

(9) The method for stabilizing a heme protein according to (8), wherein the concentration of the disulfonic acid or a salt thereof is 0.001 mol/L or more and 0.3 mol/L or less.

(10) An immunoassay method for a heme protein, comprising a step of bringing a heme protein into contact with an anti-heme protein antibody in the presence of a disulfonic acid or a salt thereof.

This description includes part or all of the contents as disclosed in Japanese Patent Application No. 2015-070667 which is a priority document of the present application.

Advantageous Effect of Invention

According to the preservative solution for a heme protein and the method for stabilizing a heme protein of the present invention, denaturation or degradation of a heme protein can be suppressed and the heme protein can be stably stored.

DESCRIPTION OF EMBODIMENTS

The present invention will be explained in detail hereinbelow.

The preservative solution for a heme protein of the present invention contains disulfonic acid or a salt thereof. Moreover, the method for stabilizing a heme protein of the present invention brings a disulfonic acid or a salt thereof into coexistence in a sample containing a heme protein.

Disulfonic acid or a salt thereof to be used in the present invention is not particularly limited and can be selected from known examples thereof. Disulfonic acid to be used in the present invention is disulfonic acid having at least one open chain or cyclic hydrocarbon group that may have a saturated or unsaturated bond, and in particular, the disulfonic acid is preferably disulfonic acid consisting of an open chain or cyclic hydrocarbon group and two sulfone groups. Disulfonic acid to be used in the present invention may have either an open chain hydrocarbon group or a cyclic hydrocarbon group, or both of these groups.

In particular, the open chain hydrocarbon group of disulfonic acid to be used in the present invention is a branched or linear hydrocarbon group. The main chain of the branched hydrocarbon group or the linear hydrocarbon group has any one of preferably 1 to 10 and more preferably 1 to 4, and further preferably 1 or 2 carbon atoms. The main chain of the branched hydrocarbon group or the linear hydrocarbon group is preferably an alkyl group, an alkenyl group, an alkynyl group, an alkylene group, an alkenylene group, or an alkynylene group. Examples of the disulfonic acid having an alkylene group include methanedisulfonic acid, 1,2-ethanedisulfonic acid (hereinafter, referred to as 1,2-EDS), 1,3-propanedisulfonic acid, 1,4-butanedisulfonic acid, 1,5-pentanedisulfonic acid, and 1,6-hexanedisulfonic acid.

Furthermore, a cyclic hydrocarbon group of disulfonic acid to be used in the present invention has preferably any one of 3 to 10 carbon atoms. The cyclic hydrocarbon group is preferably a cycloalkyl group, a cycloalkenyl group, a cycloalkynyl group, or an aryl group. In particular, the aryl group is preferably a phenylene group or a naphthylene group. Examples of disulfonic acid having a phenylene group or a naphthylene group include 1,2-benzenedisulfonic acid, 1,3-benzenedisulfonic acid, 1,4-benzenedisulfonic acid, 1,6-naphthalenedisulfonic acid, 2,6-naphthalenedisulfonic acid, and 2,7-naphthalenedisulfonic acid.

Furthermore, the cyclic hydrocarbon group may be a branched hydrocarbon group. Also, the cyclic hydrocarbon group may be substituted with 1 or more, preferably 1 to 3, or more preferably 1 to 2 nitrogen atoms. An example of disulfonic acid having a hydrocarbon group substituted with a nitrogen atom(s) is piperazine-N,N'-bis(2-ethanesulfonic acid).

Furthermore, more preferably, disulfonic acid to be used in the present invention is disulfonic acid in which two sulfone groups are bound to an open chain or cyclic hydrocarbon group. Moreover, disulfonic acid having an open chain hydrocarbon group has two sulfone groups preferably at different carbon atoms of the main chain of a branched hydrocarbon group or a linear hydrocarbon group, and more preferably at each of these ends. Disulfonic acid to be used in the present invention is preferably 1,2-ethanedisulfonic acid (1,2-EDS).

A hydrocarbon group of disulfonic acid to be used in the present invention may have a substituent such as a halogen group and/or a hydroxy group. Also, in disulfonic acid having a branched hydrocarbon group, the branched chain preferably comprises hydrocarbon. Moreover, disulfonic acid or a salt thereof to be used in the present invention is at least one or may be a mixture of two or more of the disulfonic acid or a salt thereof.

According to the present invention, a preservative solution or a sample contains a heme protein and disulfonic acid or a salt thereof, so that denaturation or degradation of the heme protein can be suppressed. In particular, according to the present invention, disulfonic acid contains ethanedisulfonic acid, so that the stability of the heme protein can be enhanced more significantly. Disulfonic acid to be used in the present invention does not adversely affect measurement, and is particularly suitable for immunoassay methods using latex immunoagglutination assay.

A salt of disulfonic acid to be used in the present invention is not particularly limited, and is a monovalent, a divalent, or a trivalent metal salt of disulfonic acid. Examples of such a salt of disulfonic acid include an alkali metal salt, an ammonium salt, an alkaline-earth metal salt, a ferrate, and an aluminum salt. Examples of an alkali metal include lithium, sodium, potassium, rubidium, and cesium. Examples of an alkaline-earth metal include calcium, strontium, barium, and radium.

The upper limit of the concentration of disulfonic acid or a salt thereof contained in the preservative solution for a heme protein or the sample containing a heme protein of the present invention is 0.3 mol/L or less, more preferably 0.2 mol/L or less, and further preferably 0.15 mol/L or less, and the lower limit of the same is 0.001 mol/L or more, more preferably 0.005 mol/L or more, further preferably 0.01 mol/L or more, and most preferably 0.02 mol/L or more. If the concentration of disulfonic acid or a salt thereof is less than 0.001 mol/L, the effect of stabilizing the heme protein will be insufficient. On the other hand, the concentration of disulfonic acid or a salt thereof higher than 0.3 mol/L will inhibit immunoreaction to affect the measurement more easily, as well as not provide the sufficient effect of stabilizing the heme protein.

A heme protein as target of the present invention and a heme protein contained in a sample of the present invention can be adequately selected from proteins containing heme as a component. Examples of heme proteins include hemoglobin, myoglobin, peroxidase and catalase. In particular, a heme protein as target of the present invention and a heme protein contained in a sample of the present invention is preferably a heme protein that is an immunological analyte, and is more preferably human hemoglobin. In immunoassay methods, maintaining the antigenicity of a detection target is important. However, the antigenicity of a heme protein can be maintained according to the present invention, enabling more accurate measurement of the heme protein. In particular, a heme protein as target of the present invention and a heme protein contained in a sample of the present invention may be hemoglobins in a biological sample, so that prevention of erroneous measurement results in diagnosis of diseases such as large bowel cancer can be expected. Examples of hemoglobin include fecal hemoglobin, hemoglobin commercially available as a reference sample or a control containing hemoglobin prepared from erythrocytes, and lyophilized hemoglobin.

Moreover, the preservative solution for a heme protein or the sample containing a heme protein of the present invention can contain a solution in which a heme protein can be dissolved. Such a solution may be a solution in which a heme protein can be dissolved and examples thereof include buffer solutions. A buffer to be used for preparation of a buffer solution is not particularly limited, as long as it has buffer capacity, and examples thereof include Good's buffer, phosphate buffer, Tris buffer, glycine buffer, and borate buffer.

Furthermore, examples of Good's buffer include 2-morpholinoethanesulfonic acid (MES) buffer, bis(2-hydroxyethyl)iminotris(hydroxymethyl)methane (Bis-Tris) buffer, N-(2-acetamide)iminodiacetate (ADA) buffer, piperazine-N,N-bis(2-ethanesulfonic acid) (PIPES) buffer, N-(2-acetamide)-2-aminoethanesulfonic acid (ACES) buffer, 3-morpholino-2-hydroxypropanesulfonic acid (MOPSO) buffer, N,N-bis(2-hydroxy ethyl)-2-aminoethanesulfonic acid (BES) buffer, 3-morpholinopropanesulfonic acid (MOPS) buffer, N-[tris(hydroxymethyl)methyl]-2-aminoethanesulfonic acid (TES) buffer, N-(2-hydroxyethyl)piperazine-N'-ethanesulfonic acid (HEPES) buffer, 3-[N,N-bis(2-hydroxyethyl)amino]-2-hydroxypropanesulfonic acid (DIPSO) buffer, 2-hydroxy-3-{[N-tris(hydroxymethyl)methyl]amino}propanesulfonic acid (TAPSO) buffer, piperazine-N,N-bis(2-hydroxypropane-3-sulfonic acid) (POPSO) buffer, N-(2-hydroxyethyl)-N-(2-hydroxy-3-sulfopropyl)piperazine (HEPPSO) buffer, N-(2-hydroxyethyl)-N'-(3-sulfopropyl)piperazine (EPPS) buffer, tricine[N-tris(hydroxymethyl)methylglycine] buffer, bicin[N,N-bis(2-hydroxyethyl)glycine] buffer, 3[N-tris(hydroxymethyl)methyl]aminopropanesulfonic acid (TAPS) buffer, 2-(N-cyclohexylamino)ethanesulfonic acid (CHES) buffer, 3-(N-cyclohexylamino)-2-hydroxypropanesulfonic acid (CAPSO) buffer, and 3-(N-cyclohexylamino)propanesulfonic acid (CAPS) buffer. Particularly, in the present invention, among examples of Good's buffer, HEPES is preferably used, the stability of a heme protein can be enhanced significantly by bringing a disulfonic acid or a salt thereof into coexistence with the heme protein.

The buffer concentration is not particularly limited, as long as it is appropriate for measurement, and ranges from 0.001 to 2.0 mol/L, preferably 0.005 to 1.5 mol/L, and further preferably 0.01 to 1.0 mol/L.

Furthermore, the pH of the preservative solution for a heme protein or the sample containing a heme protein of the present invention is preferably within a neutral range, preferably ranges from 5 to 10, and is more preferably within a range of 6 to 8. The pH of less than 5, or the pH of higher than 10 results in deteriorated stability of the heme protein, so that the heme protein will be easily denatured or degraded. The pH can be adjusted by known methods and may also be adjusted using NaOH or an appropriate buffer.

Moreover, the preservative solution for a heme protein or the sample containing a heme protein of the present invention can contain a known protein protection agent, such as a water soluble transition metal complex, a ferrocyan compound, an enzymatic degradation product of hemoglobin, transition metals, organic acid, iminocarboxylic acid, inactive proteins represented by albumin and gelatin, and sodium azide. The solution or the sample may also contain an antimicrobial agent, for example, for preventing unnecessary microbial proliferation. The solution or the sample may further contain a salt, an aggregation accelerating agent, and other components, if necessary, unless the advantageous effects of the invention are not disturbed. According to the present invention, the stability of a heme protein can be enhanced by the present invention in cooperation with a conventional protein protection agent, an antimicrobial agent, or the like without inhibiting the action of the conventional protein protection agent, the antimicrobial agent, or the like.

Furthermore, when the preservative solution for a heme protein or the sample containing a heme protein of the present invention contains albumin, bovine albumin, equine albumin, porcine albumin, sheep albumin, rabbit albumin, human albumin, rat albumin or the like can be used, and a serum containing albumin can also be used. The concentration of albumin in the preservative solution for a heme protein or the sample containing a heme protein of the present invention ranges from 0.0005 to 2.0 w/v %, and more preferably ranges from 0.01 to 0.5 w/v %.

A measurement method for a heme protein is not particularly limited, and is an immunoassay method using an anti-heme protein antibody (antibody specifically binding to a heme protein), and is preferably an immunoassay method using an anti-human hemoglobin antibody. Specifically, such a method involves, in a sample, bringing a heme protein (for example, human hemoglobin) into contact with an anti-heme protein antibody (for example, anti-human hemoglobin antibody) in the presence of disulfonic acid or a salt thereof, causing an antigen-antibody reaction, and detecting or measuring a heme protein in the sample based on the resulting immunocomplex. When a heme protein is human hemoglobin, examples of immunoassay methods for human hemoglobin include: single radial immunodiffusion that involves confirming the expression of a precipitin line by an immunocomplex formed by binding of an anti-human hemoglobin antibody and human hemoglobin in a test sample in an agar plate; a latex immunoagglutination assay using latex particles sensitized with an anti-human hemoglobin antibody; an enzyme immunoassay or a radioimmunoassay using an anti-human hemoglobin antibody labeled with an enzyme or a radioactive element; a gold colloid agglutination colorimetric method using gold colloid particles sensitized with an anti-human hemoglobin antibody; and an immunochromatography using an anti-human hemoglobin antibody labeled with a metal colloid or the like and a capture antibody for capturing an immunocomplex of the anti-human hemoglobin antibody and human hemoglobin in a membrane such as a nitrocellulose membrane. Specifically, the latex immunoagglutination assay involves reacting latex particles sensitized with an anti-human hemoglobin antibody with human hemoglobin in a sample, and measuring human hemoglobin based on changes in turbidity resulting from latex agglutination due to the formation of an immunocomplex. Moreover, immunochromatography involves, in a membrane such as a nitrocellulose membrane, supplying a sample, reacting human hemoglobin in the sample with an anti-human hemoglobin antibody at a labeling reagent-retaining part for retaining the anti-human hemoglobin antibody labeled with a metal colloid or the like, so as to form an immunocomplex, causing the immunocomplex to move within the membrane by capillary phenomenon, causing the immunocomplex to be captured by a capture antibody immobilized at a predetermined position of the membrane, and detecting human hemoglobin based on coloration resulting from the capture. Through the use of the preservative solution for a heme protein or the sample containing a heme protein of the present invention containing disulfonic acid or a salt thereof, any of these measurement methods can protect the antigenic activity of a heme protein and suppress errors in the measurement results.

The preservative solution for a heme protein of the present invention can be used as a solution for storing a heme protein in various applications. For example, the solution can be used as a solution for dissolving a heme protein derived from a biological sample such as feces, urine, and blood, or a solution such as a diluent and an extract solution. In particular, the solution is useful as a diluent for stool specimens in a test for detection of a heme protein, such as a fecal occult blood test.

Furthermore, the preservative solution for a heme protein of the present invention may contain a heme protein as target of the above present invention, and can be used as various solutions containing heme proteins. Similarly, the method for stabilizing a heme protein of the present invention can be applied to various samples containing heme proteins. For example, the preservative solution for a heme protein and the sample containing a heme protein of the present invention can be used as a reference sample containing a heme protein, a control sample containing a heme protein, and the like, and particularly as a reference sample containing a heme protein or a control sample containing the same to be used for calibration or precision control for an automatic analyzer. Even when a reference sample and a control sample containing heme proteins are stored for a long time period, the resulting measurement values of the heme proteins are required to remain unchanged. According to the present invention, denaturation or degradation of heme proteins in a reference sample and a control sample can be suppressed, even when the samples are stored at a relatively high temperature, so that the invention can contribute to the stabilization of the measurement values of heme proteins. Therefore, the preservative solution for a heme protein and the sample containing a heme protein of the present invention are suitable as a reference sample and a control sample containing heme proteins.

Furthermore, the preservative solution for a heme protein of the present invention can be provided as a kit for immunoassay of heme proteins (e.g., human hemoglobin), which is used for a fecal occult blood test, for example. This kit can contain, in addition to the preservative solution for a heme protein of the present invention, a sample storage container such as a feces collection container and an instruction manual for the kit, and, when an immunoassay method is a latex immunoagglutination assay, a latex solution sensitized with an anti-heme protein antibody, a diluent, and the like, or when an immunoassay method is immunochromatography, an immunochromatography device (e.g., membrane, such as nitrocellulose membrane supported by a support having a sample-supplying part, a labeling reagent-retaining part for retaining an anti-heme protein antibody labeled with a metal colloid or the like, and a detection part containing a capture antibody immobilized at a predetermined position), and the like.

The present invention will be further described specifically by referring to examples, but the present invention is not limited by these examples.

EXAMPLES

Example 1

A solution (pH7.0) containing 0.3 w/v % bovine serum albumin, NaOH, 0.05 mol/L phosphate buffer solution as a buffer solution, and pure water as the remainder was prepared. 1,2-EDS as an additive was added, to the solution in such an amount as to give each concentration (0.01 to 0.2 mol/L) listed in Table 1, thereby preparing a solution at each concentration. Hemolytic hemoglobin was added to 10 mL of the prepared solutions in such an amount as to give a 600 ng/mL sample.

Immediately after addition of hemoglobin, the hemoglobin concentration (concentration immediately after addition) of each sample was measured. Subsequently, each sample was stored at 37° C. With the time of adding hemoglobin designated as 0 hour of storage, hemoglobin concentration of each sample was measured after 6 hours of storage and after 24 hours of storage (concentration after 6 hours of storage and concentration after 24 hours of storage).

Hemoglobin concentration was measured using an OC sensor DIANA analyzer (Eiken Chemical Co., Ltd) and a dedicated reagent (OC-Hemodia Auto III: Eiken Chemical Co., Ltd) based on the measurement principle, a latex agglutination reaction; that is, a type of immunoassay method. Specifically, 35 µL of the sample was collected and used as a test solution, and then 60 µL of latex (latex solution sensitized with 20 vol % anti-human hemoglobin rabbit polyclonal antibody) and 300 µL of diluent (11.92 mg/mL HEPES) were added to the test solution, followed by measurement of absorbance at a wavelength of 660 nm. Based on a previously produced calibration curve, hemoglobin concentration in the test solution was determined from the thus obtained measurement value. Measurement was performed in triplicate for each sample, the mean value of the measurement results was employed as the hemoglobin concentration of each sample.

From the thus measured hemoglobin concentrations, the residual percentages of hemoglobin were found based on the following formula.

Residual percentage [%] of hemoglobin after 6 hours of storage or after 24 hours of storage=100×hemoglobin concentration [ng/mL] after 6 hours of storage or after 24 hours of storage/concentration [ng/mL] immediately after addition in control sample.

Specifically, the residual percentage of hemoglobin of each sample is a relative value with the hemoglobin concentration (immediately after addition) in a control sample designated as 100%. The control sample in this example was a phosphate buffer solution (containing no 1,2-EDS) containing bovine serum albumin and NaOH, and the concentration immediately after addition in the control sample was 583 ng/mL. The results are shown in Table 1.

TABLE 1

| Buffer solution | Additive | Additive Concentration [mM] | Residual percentage [%] After 6 hours of storage | Residual percentage [%] After 24 hours of storage |
|---|---|---|---|---|
| Phosphoric acid (control) | None | 0 | 49.4 | 7.1 |
| Phosphoric acid | 1,2-EDS | 10 | 52.5 | 7.5 |
| Phosphoric acid | 1,2-EDS | 20 | 56.3 | 9.0 |
| Phosphoric acid | 1,2-EDS | 40 | 61.9 | 12.8 |
| Phosphoric acid | 1,2-EDS | 60 | 59.7 | 12.3 |
| Phosphoric acid | 1,2-EDS | 100 | 65.4 | 16.6 |
| Phosphoric acid | 1,2-EDS | 150 | 71.5 | 24.3 |
| Phosphoric acid | 1,2-EDS | 200 | 46.2 | 7.9 |

(Note)
Residual percentage is a relative value with the concentration immediately after addition (583 ng/mL) in a control sample designated as 100%.

As shown in Table 1, samples containing the disulfonic acid, 1,2-EDS, exhibited residual percentages after 6 hours of storage and after 24 hours of storage higher than those of the control sample, indicating that 1,2-EDS had the effect of stabilizing hemoglobin. Moreover, the residual percentages were found to be higher with the increasing concentration of 1,2-EDS added, indicating that the increasing 1,2-EDS concentration enhanced the effect of stabilizing hemoglobin.

Example 2

Samples were prepared in a manner similar to Example 1 except that 0.05 mol/L N-(2-hydroxyethyl)piperazine-N'-ethanesulfonic acid (hereinafter, referred to as HEPES) was used instead of a phosphate buffer solution and that 1,2-EDS was added in such an amount as to give each concentration (0.005 to 0.2 mol/L) listed in Table 2, and then hemoglobin concentrations were measured. The results are shown in Table 2. In addition, the residual percentage of each sample was represented by a relative value with the concentration immediately after addition (576 ng/mL) in a control sample (HEPES buffer solution (containing no 1,2-EDS) containing bovine serum albumin and NaOH) designated as 100%.

TABLE 2

| Buffer solution | Additive | Additive Concentration [mM] | Residual percentage [%] After 6 hours of storage | Residual percentage [%] After 24 hours of storage |
|---|---|---|---|---|
| HEPES (control) | None | 0 | 61.8 | 11.9 |
| HEPES | 1,2-EDS | 5 | 64.3 | 14.0 |
| HEPES | 1,2-EDS | 10 | 65.2 | 16.6 |
| HEPES | 1,2-EDS | 20 | 67.1 | 18.1 |
| HEPES | 1,2-EDS | 40 | 68.5 | 19.7 |
| HEPES | 1,2-EDS | 60 | 71.3 | 20.8 |
| HEPES | 1,2-EDS | 100 | 72.4 | 21.6 |
| HEPES | 1,2-EDS | 150 | 72.8 | 20.4 |
| HEPES | 1,2-EDS | 200 | 73.1 | 21.8 |

(Note)
Residual percentage is a relative value with the concentration immediately after addition (576 ng/mL) in a control sample designated as 100%.

As shown in Table 2, samples containing the disulfonic acid, 1,2-EDS, exhibited residual percentages after 6 hours of storage and after 24 hours of storage higher than those of the control sample, indicating that 1,2-EDS had the effect of stabilizing hemoglobin. In particular, because of containing HEPES and 1,2-EDS, even a sample having the concentration of 1,2-EDS added of as low as 5 mM was found to have high residual percentage after 6 hours of storage and after 24 hours of storage. Moreover, a higher residual percentages was found with the increasing concentration of 1,2-EDS added, indicating that the increasing 1,2-EDS concentration enhanced the effect of stabilizing hemoglobin.

Example 3

Samples were prepared in a manner similar to Example 1 except that 0.05 mol/L HEPES, 0.05 mol/L piperazine-N,N'-bis(2-ethanesulfonic acid) (hereinafter, referred to as PIPES) or 0.05 mol/L 2-morpholinoethanesulfonic acid (hereinafter, referred to as MES) was used instead of a phosphate buffer solution, and that 1,2-EDS was added in such an amount as to give each concentration listed in Table 3, and then hemoglobin concentrations were measured. The results are shown in Table 3. In addition, the residual percentage of each sample was represented by a relative value with the concentration immediately after addition (583 ng/mL) in a control sample (phosphate buffer solution (containing no 1,2-EDS) containing bovine serum albumin and NaOH) designated as 100%.

TABLE 3

| Buffer solution | Additive | Additive Concentration [mM] | Residual percentage [%] | |
| --- | --- | --- | --- | --- |
| | | | After 6 hours of storage | After 24 hours of storage |
| Phosphoric acid (control) | None | 0 | 49.4 | 7.1 |
| Phosphoric acid | 1,2-EDS | 20 | 56.3 | 9.0 |
| HEPES | None | 0 | 46.3 | 9.3 |
| HEPES | 1,2-EDS | 20 | 67.6 | 20.2 |
| PIPES | None | 0 | 50.4 | 9.2 |
| PIPES | 1,2-EDS | 20 | 63.6 | 14.3 |
| MES | None | 0 | 54.6 | 11.7 |
| MES | 1,2-EDS | 20 | 65.9 | 18.7 |

(Note)
Residual percentage is a relative value with the concentration immediately after addition (583 ng/mL) in a control sample designated as 100%.

As shown in Table 3, the effect of stabilizing hemoglobin exhibited by 1,2-EDS was confirmed also in samples containing different buffer solutions. In particular, samples containing HEPES and 1,2-EDS exhibited residual percentages after 6 hours of storage and after 24 hours of storage significantly higher than those of a sample containing HEPES as a buffer solution but containing no 1,2-EDS, indicating that the samples containing HEPES and 1,2-EDS had extremely high effect of suppressing denaturation or degradation of hemoglobin, as well as suggesting that the same can stabilize hemoglobin in the long term. Further, a sample containing HEPES and 1,2-EDS exhibited residual percentages after 6 hours of storage and after 24 hours of storage higher than those of a sample containing Good's buffer (PIPES or MES) and 1,2-EDS, and was found to have more enhanced effect of suppressing denaturation or degradation of hemoglobin, indicating that it has a synergistic effect of stabilizing hemoglobin.

Example 4

Samples were prepared in a manner similar to Example 1 except that 1,4-butanedisulfonic acid (hereinafter, referred to as 1,4-BDS), 2,6-naphthalenedisulfonic acid (hereinafter, referred to as 2,6-NDS) or PIPES, instead of 1,2-EDS, was added in such an amount as to give each concentration listed in Table 4, and that 0.05 mol/L HEPES was used instead of a phosphate buffer solution, and then hemoglobin concentrations were measured. The results are shown in Table 4. In addition, the residual percentage of each sample was represented by a relative value with the concentration immediately after addition (548 ng/mL) in a control sample (phosphate buffer solution (containing no disulfonic acid) containing bovine serum albumin and NaOH) designated as 100%.

TABLE 4

| Buffer solution | Additive | Additive Concentration [mM] | Residual percentage [%] | |
| --- | --- | --- | --- | --- |
| | | | After 6 hours of storage | After 24 hours of storage |
| Phosphoric acid (control) | None | 0 | 49.8 | 6.2 |
| Phosphoric acid | 1,4-BDS | 50 | 68.3 | 14.5 |
| Phosphoric acid | 1,4-BDS | 150 | 69.9 | 18.4 |
| Phosphoric acid | 2,6-NDS | 50 | 55.7 | 11.1 |
| Phosphoric acid | PIPES | 50 | 58.4 | 10.4 |
| HEPES | None | 0 | 64.9 | 12.5 |
| HEPES | 1,4-BDS | 150 | 74.7 | 28.4 |

(Note)
Residual percentage is a relative value with the concentration immediately after addition (548 ng/mL) in a control sample designated as 100%.

As shown in Table 4, the disulfonic acid, 1,4-BDS, 2,6-NDS, and PIPES were found to have the effect of stabilizing hemoglobin.

Comparative Example 1

Samples were prepared in a manner similar to Example 1 except that 8-anilino-1-naphthalenesulfonate (hereinafter, referred to as ANS) or sodium 2-mercaptoethanesulfonate (hereinafter, referred to as MESS) was added in such an amount as to give 0.01 mol/L instead of 1,2-EDS, and then hemoglobin concentrations were measured. The results are shown in Table 5. In addition, the residual percentage of each sample was represented by a relative value with the concentration immediately after addition (583 ng/mL) in a control sample (phosphate buffer solution (containing no additive) containing bovine serum albumin and NaOH) designated as 100%.

TABLE 5

| Buffer solution | Additive | Additive Concentration [mM] | Residual percentage [%] | |
| --- | --- | --- | --- | --- |
| | | | After 6 hours of storage | After 24 hours of storage |
| Phosphoric acid (control) | None | 0 | 49.4 | 7.1 |
| Phosphoric acid | 1,2-EDS | 10 | 52.5 | 7.5 |
| Phosphoric acid | ANS | 10 | 2.6 | 2.5 |
| Phosphoric acid | MESS | 10 | 33.4 | 3.3 |

(Note)
Residual percentage is a relative value with the concentration immediately after addition (583 ng/mL) in a control sample designated as 100%.

As shown in Table 5, denaturation or degradation of hemoglobin might have proceeded in a sample containing not disulfonic acid but sulfonic acid.

Therefore, it was demonstrated that a preservative solution and a sample containing disulfonic acid such as 1,4-BDS, 2,6-NDS, and 1,2-EDS can maintain the residual percentages of hemoglobin after 6 hours of storage and after 24 hours of storage at high levels, even when stored at a high temperature of 37° C. These results indicate that the preservative solution and the sample containing disulfonic acid of the present invention suppress denaturation or degradation of hemoglobin and have the effect of stabilizing hemoglobin, even subjected to temperature rise and the passage of time.

Moreover, when a stool specimen was added to each sample of Examples 1 to 4 and Comparative example 1 and similar measurements were performed, tendency similar to that of measurement results in Examples 1 to 4 and Comparative example 1 was observed.

It was revealed that according to the preservative solution for a heme protein containing disulfonic acid or a salt thereof and the method for stabilizing a heme protein of the present invention, denaturation or degradation of a heme protein can be suppressed and the heme protein can be stabilized.

INDUSTRIAL APPLICABILITY

According to the preservative solution for a heme protein and the method for stabilizing a heme protein of the present invention, denaturation or degradation of a heme protein can be suppressed, and the heme protein can be stably stored. Specifically, heme proteins such as those in a diluent for stool specimens in a fecal occult blood test, a reference sample containing a heme protein, and a control sample containing a heme protein can be stably stored.

All publications, patents, and patent applications cited herein are incorporated herein by reference in their entirety.

The invention claimed is:

1. A method for stabilizing a heme protein, comprising the steps of:
    bringing a disulfonic acid or a salt thereof into coexistence in a sample comprising a heme protein; and
    measuring the heme protein with an anti-heme protein antibody,
    wherein the disulfonic acid or a salt thereof has at least one of an open chain hydrocarbon group or a cyclic hydrocarbon group, and
    the disulfonic acid or a salt thereof is at least one selected from the group consisting of:
    a disulfonic acid or a salt thereof in which the open chain hydrocarbon group is a branched or linear hydrocarbon group, does not have a cyclic hydrocarbon group, and the main chain of the branched open chain hydrocarbon group or the linear open chain hydrocarbon group has any one of 1 to 10 carbon atoms; and
    a disulfonic acid or a salt thereof selected from the group consisting of 1,2-benzenedisulfonic acid, 1,3-benzenedisulfonic acid, 1,4-benzenedisulfonic acid and a disulfonic acid having a naphthylene group, or a salt thereof.

2. The method of claim 1, wherein the disulfonic acid consists of an open chain or cyclic hydrocarbon group and two sulfone groups.

3. The method of claim 1, wherein the disulfonic acid has a substituent and the substituent is a halogen group and/or a hydroxy group.

4. A method for stabilizing a heme protein, comprising:
    bringing a disulfonic acid or a salt thereof into coexistence in a sample comprising a heme protein,
    wherein the disulfonic acid or a salt thereof is at least one selected from the group consisting of methanedisulfonic acid, ethanedisulfonic acid, propanedisulfonic acid, butanedisulfonic acid, naphthalenedisulfonic acid, and a salt thereof.

5. The method of claim 1, further comprising bringing N-(2-hydroxyethyl)piperazine-N'-ethanesulfonic acid into coexistence in the sample comprising the heme protein.

6. The method of claim 1, wherein the concentration of the disulfonic acid or a salt thereof is 0.001 mol/L or more and 0.3 mol/L or less.

7. The method of claim 4, further comprising bringing N-(2-hydroxyethyl)piperazine-N'-ethanesulfonic acid into coexistence in the sample comprising the heme protein.

8. The method of claim 4, wherein the concentration of the disulfonic acid or a salt thereof is 0.001 mol/L or more and 0.3 mol/L or less.

* * * * *